United States Patent [19]

West

[11] Patent Number: 5,009,594

[45] Date of Patent: Apr. 23, 1991

[54] DISPOSABLE TRANSFER JIG ASSEMBLY

[75] Inventor: Weldon D. West, Mission Viejo, Calif.

[73] Assignee: Denar Corporation, Anaheim, Calif.

[21] Appl. No.: 381,466

[22] Filed: Jul. 18, 1989

[51] Int. Cl.$^5$ .............................................. A61C 19/04
[52] U.S. Cl. ....................................................... 433/73
[58] Field of Search ....................... 433/73, 56, 57, 58, 433/59, 60, 68, 69

[56] References Cited

U.S. PATENT DOCUMENTS 4,734,033 3/1988 Huffman ............................... 433/60
4,836,779 6/1989 Beu ......................................... 433/73

FOREIGN PATENT DOCUMENTS 3540756 5/1987 Fed. Rep. of Germany ........ 433/68

Primary Examiner—Cary E. Stone
Attorney, Agent, or Firm—Cahill, Sutton & Thomas

[57] ABSTRACT

An adjustable transfer jig assembly interconnecting a face bow and a bitefork is positionally fixed after locating the bitefork relative to the face bow. Clamp blocks of plastic interconnecting plastic rods forming the jig assembly include slots for receiving and wicking about the encircled rods a fast setting adhesive to lockingly position the rods linearly and angularly with respect to one another and fix the transfer jig assembly. Subsequent detachment of the face bow will permit mounting of the bitefork upon an articulator in a predetermined relationship by attaching the transfer jig assembly to an articulator mounted index block.

8 Claims, 1 Drawing Sheet

DISPOSABLE TRANSFER JIG ASSEMBLY

BACKGROUND OF THE INVENTION

1. Field of the Invention

The present invention relates to dental instruments and, more particularly, to bitefork transfer jig assemblies.

2. Description of the Prior Art

Transfer jig assemblies are used to repetitively determine the position of a bitefork relative to certain indices of a patient in order to develope a dental prosthetic. Existing transfer jig assemblies are generally metallic and include machined parts. In particular, metallic rods are interconnected by clamping blocks having finger tightenable screws threadedly engaging the blocks to clamp the rods therein. The bitefork is positionally established relative to a face bow which represents a reference point for the bitefork. After the face bow is positionally aligned and the bitefork located relative thereto through positional adjustment of the rods of the transfer jig assembly, the components of the transfer jig assembly must be lockingly secured to one another.

To lockingly secure the transfer jig assembly, each of the finger screws must be tightened with careful attention to maintain the facebow in its reference location. The time required to tighten the finger screws is of significance and increases the likelihood of misalignment during the tightening process. Accordingly, great accuracy is difficult to obtain without a great deal of attention by a dentist or technician.

To make the dental prosthetic, the transfer jig assembly, including the attached bitefork, is delivered to a dental laboratory. A dental technician mounts the transfer jig assembly upon a mounting block attachable to an articulator in accordance with an index. The work attendant the dental prosthetic may now be performed. Because such transfer jig assembly is relatively expensive, it must be returned to the dental office for reuse. This lack of disposability requires stockpiling in a dental office of a plurality of reuseable transfer jig assemblies with attendant high overhead costs.

Cleaning and sterilization of transfer jig assemblies prior to use is expensive and time consuming. Failure to sterilize may expose both patients and medical personnel to possibly incurable and probably fatal diseases.

SUMMARY OF THE INVENTION

An adjustable transfer jig assembly positions a bitefork in relation to a detachably attachable face bow. Once the relationship is set, a quick setting adhesive is applied to blocks interconnecting the rods of the transfer jig assembly to lockingly secure the rods in place and set the assembly. The block and rods may be formed of manmade plastic or other material readily adherable to one another with a quick setting adhesive. To ensure sufficient strength of the adhered joints, slots are formed in the blocks to encourage wicking of the adhesive.

It is therefore a primary object of the present invention to provide a rapidly settable transfer jig assembly.

Another object of the present invention is to provide an adjustable transfer jig assembly for setting the relationship of a bitefork with respect to a reference point.

Another object of the present invention is to provide a transfer jig assembly which is rapidly lockingly set.

Still another object of the present invention is to provide a transfer jig assembly which eliminates the need for manipulation of any part of the assembly during setting of same.

A further object of the present invention is to provide a disposable unit of use transfer jig assembly.

A still further object of the present invention is to provide an inexpensive transfer jig assembly.

A yet further object of the present invention is to provide a method for setting a transfer jig assembly.

A yet further object of the present invention is to provide a method for using a prewaxed bitefork.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which.

DESCRIPTION OF THE PREFERRED EMBODIMENT

Figure 1:
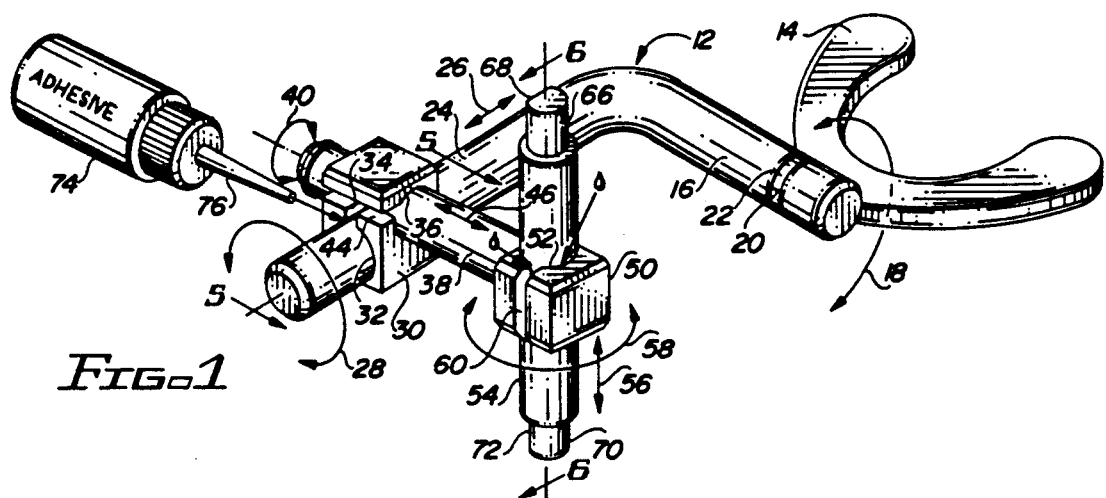
FIG. 1 is a perspective view of a transfer jig assembly.
Figure 2:
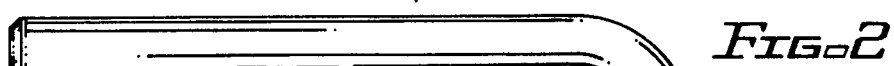
FIG. 2 is a top view of a dentulous bitefork.

Referring to FIG. 1, there is shown a transfer jig assembly 10, for positionally supporting a bitefork rod 12 having a bitefork 14 molded at the end thereof. The bitefork is angularly adjustably molded upon arm 16 of the bike fork rod, as depicted by arrow 18. Indicia 20 is disposed upon an exposed member 22. Accordingly, rotation of the bitefork about the longitudinal axis of arm 24 can be determined and may be reproduced by correlating the position of indicia 20 with a corresponding reference point upon the arm which lines up with the patient's midsagittal plane. Arm 24 of bitefork rod 12 is set at a 90° angle to arm 16, as shown in FIG. 2.

Figure 5:
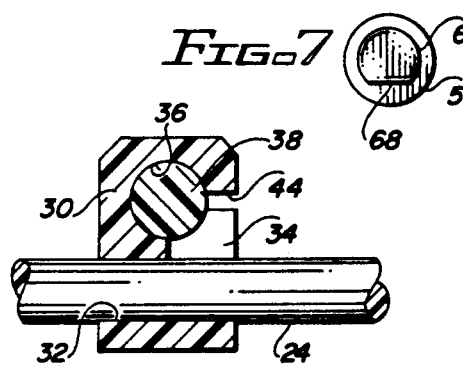
FIG. 5 is a partial cross sectional view taken along lines 5—5, as shown in FIG. 1.

Arm 24 is slidably and rotatably mounted within clamp block 30, as depicted by arrows 26,28, respectively. A cylindrical passageway 32 may be formed within the clamp block for this purpose. A slot 34 interconnects with cylindrical passageway 32 to provide access to the surface of the passageway and to the cylindrical surface of arm 24 disposed within the clamp block. The clamp block includes a second cylindrical passageway 36 displaced from and normal to cylindrical passageway 32, as shown in FIG. 5. A support rod 38 is rotatably and linearly mounted within cylindrical passageway 36, as depicted by arrows 40 and 46, respectively in FIG. 1. A slot 44 interconnects with cylindrical passageway 36 to provide access to the cylindrical surface of support rod 38 and the surface of the encircling cylindrical passageway.

Figures 6, 7:
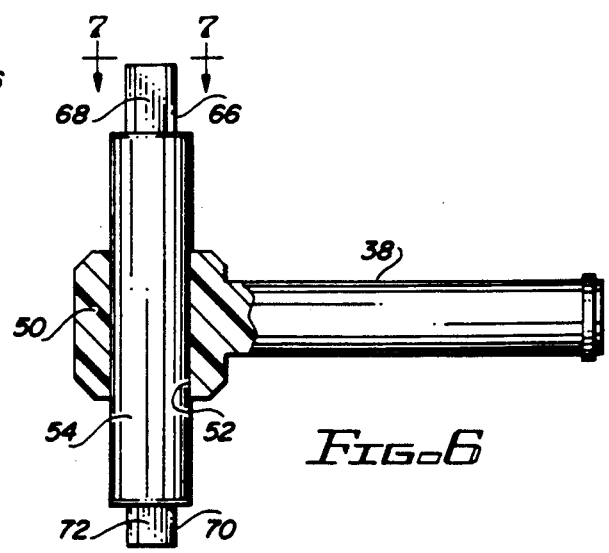
FIG. 6 is a cross sectional view taken along lines 6—6, as shown in FIG. 1.
FIG. 7 is a top view taken along lines 7—7, as shown in FIG. 6.

Support rod 38 includes a block 50 secured to one end thereof, as shown in FIG. 6. The block includes a cylindrical passageway 52 for receiving a support rod 54. The support rod is rotatably and linearly adjustable within cylindrical passageway 52, as depicted by arrows 56 and 58, respectively in FIG. 1. A slot 60 interconnects with the cylindrical passageway to provide access to the cylindrical surface of support rod 54 and the interior surface of the cylindrical passageway.

Ends 66 and 70 of support rod 54 is necked down, as depicted in FIGS. 6 and 7, and includes flats 68 and 72. The necked down end and flat serve to attach the transfer jig assembly to a face bow in indexed relationship. The other end 70 serves to mount the transfer jig assembly upon a block attachable to an articulator in conformance with an articulator associated index. In this manner, end 66 positions the transfer jig assembly with respect to a face bow to permit establishment of a jig to set the bitefork and to locate the bitefork upon an articulator in a predetermined relationship commensurate with the dental anatomy of the patient for whom a dental prosthetic is to be fabricated.

In operation, a face bow is mounted upon a patient in a conventional manner with the transfer jig assembly mounted thereto to locate the bitefork within the patient's mouth. Upon establishing the position of the bitefork relative to the face bow, the adjustable transfer jig assembly must be fixated. Such fixation is accomplished by applying an adhesive within slot 34, as depicted by adhesive container 74 and its delivery tube 76. Upon dispensing one or more drops of quick setting adhesive within slot 34, the adhesive will tend to wick into cylindrical passageway 32 intermediate to the surface of the passageway and the surface of arm 24. Upon setting, arm 24 will become fixed with respect to clamp block 30. Upon application of one or more drops of adhesive within slot 44, the adhesive will flow and wick into cylindrical passageway 36 between the surface of the passageway and the surface of support rod 38. On setting, the adhesive will fix the relationship of support rod 38 with respect to clamp block 30. Thus, the positional relationship between fork support rod 12 and support rod 38 is fixed. Upon applying one or more drops of adhesive in slot 60 of clamp block 50. The adhesive will flow and wick into cylindrical passageway 52 intermediate the surface of the passageway and the surface of support rod 54. On setting of the adhesive, the support rod will become positionally fixed with respect to clamp block 50. The three rods of the transfer jig assembly will now be positionally fixed with respect to one another and the positional relationship between necked down ends 66 and 70 with bitefork 14 will be permanently established.

Figure 3:
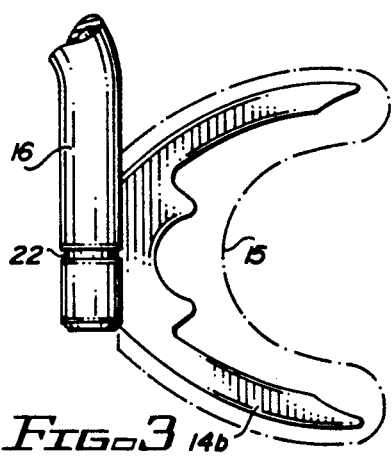
FIG. 3 is a partial view of an edentulous bitefork.
Figure 4:
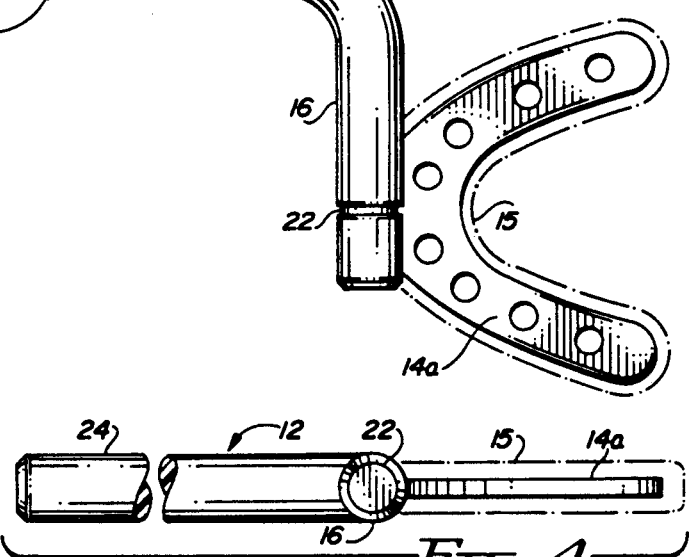
FIG. 4 is a partial side view of a pre waxed bitefork.

Block 50 is shown as being formed a part of support rod 38. However, it may be an independent element, like clamp block 30, if justified by manufacturing or operational requirements or parameters. As shown in FIGS. 2, 3 and 4, the bitefork may be a dentulous bitefork 14a or an edentulous bitefork 14b. A wax preform 15 may be fabricated and mounted upon either type of bitefork prior to use.

It may be appreciated that the application of an adhesive into each of the slots requires no manipulation of the transfer jig assembly. Accordingly, the likelihood of repositioning any of the rods with respect to any of the clamp blocks during fixation is unlikely to occur. Furthermore, the steps of applying adhesive to the two slots described can be performed very rapidly. By using any one of the many available rapidly curing or rapidly setting adhesives, such as a cyanoacrylate adhesive, setting can occur in a matter of seconds; moreover, aerobic or anaerobic adhesives may be used. Accordingly, the time that the positional relationship between the face bow and the bitefork must be maintained immobile is relatively short, which is of benefit to both the patient and the dentist or technician setting the transfer jig assembly.

It is preferable that transfer jig assembly 10 be disposable to eliminate the need for return of same by dental laboratories to a dental office. This will eliminate the need to stockpile the reuseable transfer jig assemblies and the attendant overhead costs associated therewith will be eliminated.

The spreading of contagious diseases is always a problem in any facility rendering medical care. While sterilization procedures for dental instruments are well known and have been used for many years, it is preferable to avoid the need for sterilization due to repeated use of instruments. By having the transfer jig assembly be a disposable unit of use item, it can be packaged in sterile condition within a sealed pouch container. Prior to use and softening the wax, such container can be opened and the transfer jig assembly will be sterile and ready for use.

To be disposable, the transfer jig assembly must necessarily be relatively low in cost. Moreover, the transfer jig assembly must also be sufficiently robust to maintain a set and such set can only be accomplished if an adhesive compatible with the material of the transfer jig assembly is used and which adhesive provides very rapid curing or setting time. Plastics, of a type well known to those skilled in the art, are readily available for use in conjunction with fast setting or curing adhesives, such as cyanoacrylate. The components of the transfer jig assembly illustrated in FIG. 1 are relatively straightforward in structure and readily formable by conventional plastic fabrication techniques well known to those skilled in the art. Accordingly, the transfer jig assembly may be made of relatively inexpensive materials by commensurately inexpensive fabrication techniques to render a device sufficiently low in cost to permit it to be disposable.

By being disposable, transfer jig assembly 10 will avoid the cleaning, sterlizing, packaging and transport costs attendant return of such devices from a dental laboratory to a dental office. The costs attendant sterilizing the related prior art devices will be avoided and the integrity of the transfer jig assembly can be maintained as high as that of related existing devices and yet the set up time can be substantially reduced as a result of the rapid fixation of the moveable and adjustable components.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. An adhesive fixatable disposable transfer jig apparatus for using in preparing a dental prosthetic, said apparatus comprising in combination:
   (a) a bitefork having an arm extending therefrom;
   (b) a first support rod;
   (c) a first clamp block for interconnecting said arm with said first support rod and for fixating said arm with said first support rod, said first clamp block including a first cylindrical passageway for receiving said arm, a first slot extending from said first cylindrical passageway for accommodating a flow of adhesive intermediate said arm and said first cylindrical passageway, a second cylindrical passageway for receiving said first support rod, a second slot extending from said second cylindrical passageway for accommodating a flow of adhesive intermediate said first support rod and said second cylindrical passageway;

(d) a second support rod;

(e) a second clamp block for interconnecting said first support rod with said second support rod, said second clamp block being formed as an integral part of said second support rod and inseparable therefrom; said second clamp block including a third cylindrical passageway for receiving said second support rod, a third slot extending from said third cylindrical passageway for accommodating a flow of adhesive intermediate said third support rod and said third cylindrical passageway; and (f) said first and second slots being interconnected with one another to accommodate flow of adhesive into each of said first and second passageways upon a single application of adhesive into one of said first and second slots.

2. The apparatus as set forth in claim 1 wherein said first and second slots are oriented orthogonal with one another.

3. The apparatus as set forth in claim 1 wherein each of said first and second clamp blocks is of plastic.

4. The apparatus as set forth in claim 1 wherein each of said arm, first support rod and second support rod is of plastic.

5. The apparatus as set forth in claim 4 wherein each of said first and second clamp blocks is of plastic.

6. The apparatus as set forth in claim 1 wherein said first clamp block is devoid of any mechanical means for expanding or compressing either said first slot or said second slot to release or engage, respectively, said arm or said first support rod.

7. The apparatus as set forth in claim 6 wherein said second clamp block is devoid of any further mechanical means for expanding or compressing said third slot to release or engage, respectively, said second support rod.

8. The apparatus as set forth in claim 1 wherein said second clamp means is devoid of any mechanical means for expanding or compressing said third slot to release or engage, respectively, said second support rod.

* * * * *